(12) United States Patent
Panzenbeck et al.

(10) Patent No.: US 11,666,358 B2
(45) Date of Patent: Jun. 6, 2023

(54) JACKET FLEXIBLE NEEDLE ASSEMBLY

(71) Applicant: GYRUS ACMI, INC., Southborough, MA (US)

(72) Inventors: Jason T. Panzenbeck, Redmond, WA (US); Chris Ralph, Redmond, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 219 days.

(21) Appl. No.: 16/486,784

(22) PCT Filed: Feb. 22, 2017

(86) PCT No.: PCT/US2017/018787
§ 371 (c)(1),
(2) Date: Aug. 16, 2019

(87) PCT Pub. No.: WO2018/156107
PCT Pub. Date: Aug. 30, 2018

(65) Prior Publication Data
US 2020/0008837 A1    Jan. 9, 2020

(51) Int. Cl.
*A61B 17/34* (2006.01)
*A61B 17/00* (2006.01)

(52) U.S. Cl.
CPC .......... *A61B 17/3421* (2013.01); *A61B 2017/00986* (2013.01)

(58) Field of Classification Search
CPC ............ A61B 17/3421; A61B 17/3478; A61B 2017/00986; A61B 2017/00292;
(Continued)

(56) References Cited

U.S. PATENT DOCUMENTS 5,346,502 A * 9/1994 Estabrook ...... A61B 17/320068
606/169
5,617,874 A 4/1997 Baran
(Continued)

FOREIGN PATENT DOCUMENTS

CN    101816578 A    9/2010
CN    103153201 A    6/2013
(Continued)

OTHER PUBLICATIONS

International Search Report, PCT/2017/018787, dated Oct. 26, 2017.
(Continued)

*Primary Examiner* — Richard G Louis
*Assistant Examiner* — Chima U Igboko
(74) *Attorney, Agent, or Firm* — Schwegman Lundberg & Woessner, P.A.

(57) ABSTRACT

The present teachings relate generally to a medical flexible needle assembly (10), comprising a needle portion (20) disposed at a distal end (12) of the assembly; a stiff portion (30) disposed at a proximal end 14 of the assembly; an flexible portion disposed between and interconnecting the needle portion and the stiff portion, including a flex distal portion (42), a flex proximal portion (44); and a jacketing member (50) disposed about the assembly (10) over at least part of the flexible portion (40); characterized in that the jacketing member (50) includes one or more coupled regions (60) and one or more decoupled region (70), wherein in at least one or more of the one or more coupled regions (60) are located proximally, distally, or both of the flexible portion (40).

14 Claims, 5 Drawing Sheets

(58) Field of Classification Search
CPC .......... A61B 2017/003; A61B 10/0283; A61B 1/00078; A61B 1/00154; A61M 25/0054; A61M 25/0023; A61M 2025/0004; A61M 2025/0175; A61M 2025/0915
See application file for complete search history.

(56) References Cited

U.S. PATENT DOCUMENTS

| | | | |
|---|---|---|---|
| 7,540,875 | B2 | 6/2009 | Jessen |
| 2004/0073162 | A1* | 4/2004 | Bleam .................. A61M 25/09 604/103 |
| 2005/0043682 | A1 | 2/2005 | Kucklick et al. |
| 2011/0093007 | A1* | 4/2011 | Abbott ............... A61B 17/0644 606/213 |
| 2011/0196410 | A1* | 8/2011 | Besselink ............... A61F 2/013 606/191 |
| 2012/0109130 | A1* | 5/2012 | Casey ................ A61B 17/1622 606/79 |
| 2013/0006144 | A1 | 1/2013 | Clancy |
| 2013/0225997 | A1* | 8/2013 | Dillard ............... A61B 10/0233 29/896.9 |
| 2014/0276051 | A1 | 9/2014 | Hoffman |
| 2016/0153719 | A1 | 6/2016 | Tokuda et al. |
| 2016/0279388 | A1 | 9/2016 | Barrish et al. |
| 2018/0064908 | A1* | 3/2018 | Shuman ............... A61M 25/005 |

FOREIGN PATENT DOCUMENTS

| | | |
|---|---|---|
| CN | 105377324 A | 3/2016 |
| CN | 105496552 A | 4/2016 |
| CN | 105813680 A | 7/2016 |
| CN | 105979880 A | 9/2016 |
| CN | 110430829 A | 11/2019 |
| EP | 0546712 A2 | 6/1993 |
| EP | 3568094 A1 | 11/2019 |
| EP | 3568094 B1 | 4/2022 |
| JP | 2004351005 A | 12/2004 |
| JP | 2008005965 A | 1/2008 |
| JP | 2013503693 A | 2/2013 |
| JP | 2020508162 A | 3/2020 |
| JP | 6901582 B2 | 6/2021 |
| WO | 2004/030740 A | 4/2004 |
| WO | 2014/080421 A1 | 5/2014 |
| WO | 2016/153719 A1 | 9/2016 |
| WO | WO-2018156107 A1 | 8/2018 |

OTHER PUBLICATIONS

"Chinese Application Serial No. 201780087028.5, Response filed Mar. 29, 2022 to Office Action dated Dec. 16, 2021", with English claims and machine translation, 10 pgs.

"Chinese Application Serial No. 201780087028.5, Office Action dated May 9, 2022", with English translation of claims, 15 pgs.

"Chinese Application Serial No. 201780087028.5, Office Action dated Aug. 25, 2022", with English translation of claims, 10 pgs.

"Chinese Application Serial No. 201780087028.5, Office Action dated Dec. 16, 2021", with English translation of claims, 8 pgs.

"Chinese Application Serial No. 201780087028.5, Response filed Jul. 7, 2022 to Office Action dated May 9, 2022", w/ English Claims, 8 pgs.

"European Application Serial No. 17707743.5, Intention to Grant dated Sep. 30, 2021", 20 pgs.

"European Application Serial No. 17707743.5, Response to Communication pursuant to Rules 161(1) and 162 EPC filed Mar. 24, 2020", 20 pgs.

"International Application Serial No. PCT/US2017/018787, International Preliminary Report on Patentability dated Sep. 6, 2019", 8 pgs.

"International Application Serial No. PCT/US2017/018787, Written Opinion dated Oct. 26, 2017", 6 pgs.

"Japanese Application Serial No. 2019-546035, Notice of Reasons for Refusal filed Oct. 27, 2020", with English translation of claims, 16 pgs.

"Japanese Application Serial No. 2019-546035, Written Opinion filed Mar. 29, 2021", with English translation, 12 pgs.

* cited by examiner

JACKET FLEXIBLE NEEDLE ASSEMBLY

FIELD

The present teachings relate to a medical flexible needle assembly with improved performance, more particularly a jacketed medical flexible needle assembly with a locally delaminated or decoupled jacket.

BACKGROUND

There is in certain medical procedures, a generally flexible medical device or needle may be preferred over a generally rigid medical device or needle. For example, a generally flexible needle (or flexible portion of a needle assembly) may be preferred during needle insertion and needle steering in the anatomy. It is generally known, that the flexible portion can be created by scribing or etching cuts in or through the wall of the needle or by some other means. When a flexible needle is used, it is generally desirable to include a barrier or jacket over at least some portion of the flexible portion to allow for a vacuum to be maintained in the case where the cuts are all the way through the needle wall. But, it is also contemplated that it is desirable have a device that is durable and does not greatly restrict the function of the cuts. It is also contemplated that the entire assembly (e.g. needle and jacket) have a diameter as small as possible while maintaining as large an inside diameter as possible.

It may therefore be desirable to have a flexible jacketed needle that includes features that allow movement of the cuts (flexing of the needle assembly), without the loss of the benefits of the jacketing. It may be attractive to provide a flexible jacketed needle that can be mass-produced relatively inexpensively, that has a minimal number of parts, and that is durable and relatively small in diameter.

SUMMARY

The present teachings relate generally to a flexible needle assembly with a protective jacketing disposed over at least a portion of the assembly. The jacketing selectively attached to the assembly in regions that allow for an optimal balance of properties, including flexibility, durability, and performance.

The teachings herein provide for a hollow medical flexible needle assembly 10, comprising: a needle portion 20 disposed at a distal end 12 of the assembly; a stiff portion 30 disposed at a proximal end 14 of the assembly; an flexible portion 40 disposed between and interconnecting the needle portion and the stiff portion, including a flex distal portion 42, a flex proximal portion 44, and a flex intermediate portion therebetween; and a jacket layer 50 disposed about the assembly 10 over at least part of the flexible portion 40; characterized in that the jacketing member 50 includes one or more coupled regions 60 and one or more decoupled region 70, wherein in at least one or more of the one or more coupled regions 60 are located proximally, distally, or both of at least a portion of the flexible portion 40.

The teachings may also include one or more of the following: at least one of the one or more coupled regions 60 are disposed entirely outside of the flexible portion 40; at least one of the one or more coupled regions 60 are disposed within the flexible portion 40; at least one of the one or more decoupled regions 70 are disposed within the flexible portion 40; at least one of the one or more decoupled regions 70 are at least disposed over a spiral cut feature 48 and at least laterally away from the cut by a predefined amount; a third coupled region 62 is disposed between the one or more coupled regions 60; the coupled region 62 is disposed in-between a spiral cut feature 48, the spiral flex feature disposed within the flexible portion 40.

DETAILED DESCRIPTION

Figure 1:
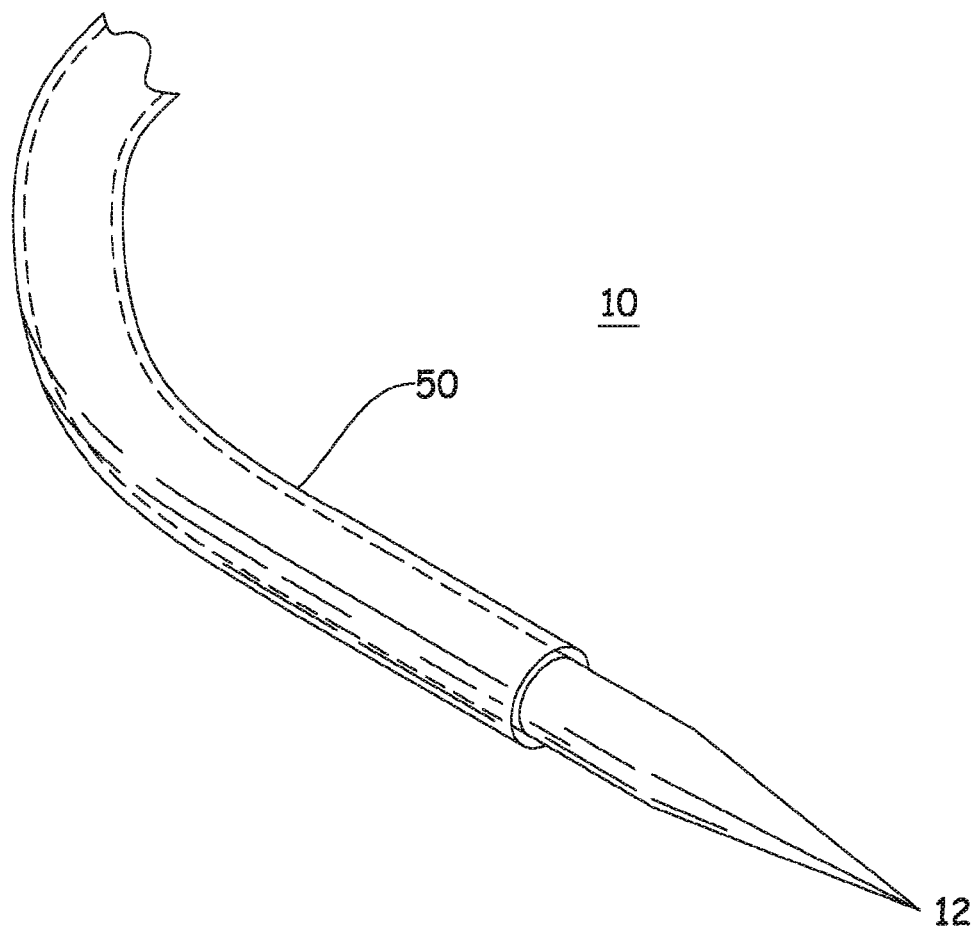
FIG. 1 is a perspective view of the distal end of a flexible needle assembly.

The explanations and illustrations presented herein are intended to acquaint others skilled in the art with the invention, its principles, and its practical application. The specific embodiments of the present invention as set forth are not intended as being exhaustive or limiting of the invention. The scope of the invention should be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description. The present teachings relate generally to a medical flexible needle assembly. Each physical element is described in more detail below.

Flexible Needle Assembly 10

It is contemplated that the medical flexible needle assembly 10, may include a number of functional segments, including but not limited to a needle portion 20; a stiff portion 30; a flexible portion 40; and a jacketing member 50 disposed about the assembly 10 over at least part of the flexible portion 40. The assembly 10 may be a single shaft (e.g. hypotube 18) covered in at least one portion by the jacket or may be an assembly of the functional segments (e.g. needle portion, stiff portion, and flexible portion) at least partially covered by the jacket, or any combination thereof.

It is contemplated that the needle portion 20 or tissue piercing portion generally is disposed at a distal end 12 of the assembly and has a point at one end (distal end) and is solid or hollow. For the sake of this disclosure, it is assumed that the proximal end of the needle portion ends at the distal end of the flexible portion. The needle portion 20 can be generally unitary to and contiguous to the assembly or may be a separate component that is added to the assembly. In a preferred embodiment, the needle portion is contiguous to at least the flexible portion, or in other words, comprised of the same shaft or hypotube 18.

It is contemplated that the stiff portion 30 is disposed at or near proximal end 14 of the assembly. For the sake of this disclosure, it is assumed that the distal end of the stiff portion ends at the proximal end of the flexible portion. The stiff portion 30 can be generally unitary to and contiguous to the assembly or may be a separate component that is added to the assembly. It may include or be attached to other components (e.g. a handle, a guide mechanism, or similar components). In a preferred embodiment, the stiff portion is contiguous to at least the flexible portion, or in other words, comprised of the same shaft.

It is contemplated that the flexible portion 40 is disposed between and interconnects the stiff portion and the needle portion. The flex portion may be comprised a tube that has one or more cuts 48 that are cut (e.g., machine or laser) or etched into it. The flexible portion having at least a flex distal portion 42 (e.g. last portion of the cut), a flex proximal portion 44 (e.g. first portion of the cut), and a flex intermediate portion therebetween. It may also be comprised of structures, e.g. locking features and flexibility reliefs, described in international patent application PCT/US2016/019682, incorporated by reference as it relates to the ability to flex the device.

In the case of a cut, and in a preferred embodiment, the cut may have a width or kerf "K". This width K may range from about 0.01 mm to as much as about 1.0 mm. It is contemplated that the jacketing member 50 spans across the width and is not coupled to the hypotube 18 across the width in any of the embodiments.

Jacketing Member 50

The jacket member may function to protect portions of the flexible needle assembly (e.g. one or more of needle portion 20; a stiff portion 30; a flexible portion 40), and particularly to help maintain the functionality of the assembly 10 such as maintaining a vacuum and still allowing flexibility. The jacket may be made of flexible material, such as a metal, a plastic, a polymer, a material that is biocompatible, or any combination thereof. The jacket may provide support or integrity to the assembly so that the device can take and retain a sample. The jacket may also be an outer containment jacket that interfaces with the inner lumen of an endoscope or another delivery device (e.g. bronchoscope). It is contemplated for one of the potential purposes of the present invention that the jacket may function as a protective barrier for the external side (outside diameter "OD") of the flexible needle assembly. It is of particular import to have the jacket form a barrier over the flexible portion, which for example may be less smooth due to the geometry created to allow for flexibility of the needle assembly, while providing a contiguous integrity for the tube (e.g. an air/liquid tight seal). It is contemplated that the jacketing should be as thin as possible while maintaining its beneficial attributes. In a preferred embodiment, the jacket may range in thickness from about 0.005 mm to about 0.25 mm depending upon the material choice and the desired properties.

It is believed that it is commonly known that it is desirable to have the jacketing member that remains completely intact and connected to the assembly during use, particularly to maintain a seal over the flexible portion. It is believed that typical jacketing used today in this application may be constructed of a heat shrinkable polymer that is coupled (e.g. bonded) to the needle assembly along its entire length. One such jacketfixed layer material that is known and commercially available is Pebax® 2533 SA 01 MED resin, by Arkema. Pebax® 2533 SA 01 MED resin is a thermoplastic elastomer made of flexible polyether and rigid polyamide. It is contemplated that other materials may be employed, such as Polyethylene terephthalate "PET", Polyurethane "PU", and/or Polytetrafluoroethylene "PTFE".

Coupled and Uncoupled Regions 60, 70

The present invention is directed towards taking the jacketing 50 and providing for selective coupled and uncoupled regions (60,70) that allow for the movement of the cuts (flexing of the needle assembly), without the loss of the benefits of the jacketing. Surprisingly, by providing select decoupled regions, the functionality (e.g. flexibility, durability, maintaining vacuum) of the assembly can be optimized. It is believed that utilizing select decoupled regions may allow for lower stresses in the jacketing and greater stretching when the assembly is flexed. It is believed that this can increase the durability of the assembly and prevent rupture of the jacketing. This increase in decoupled region length also may reduce stiffness in the laser cut section and may allow increased angulation in the endoscope or bronchoscope.

Figure 2:
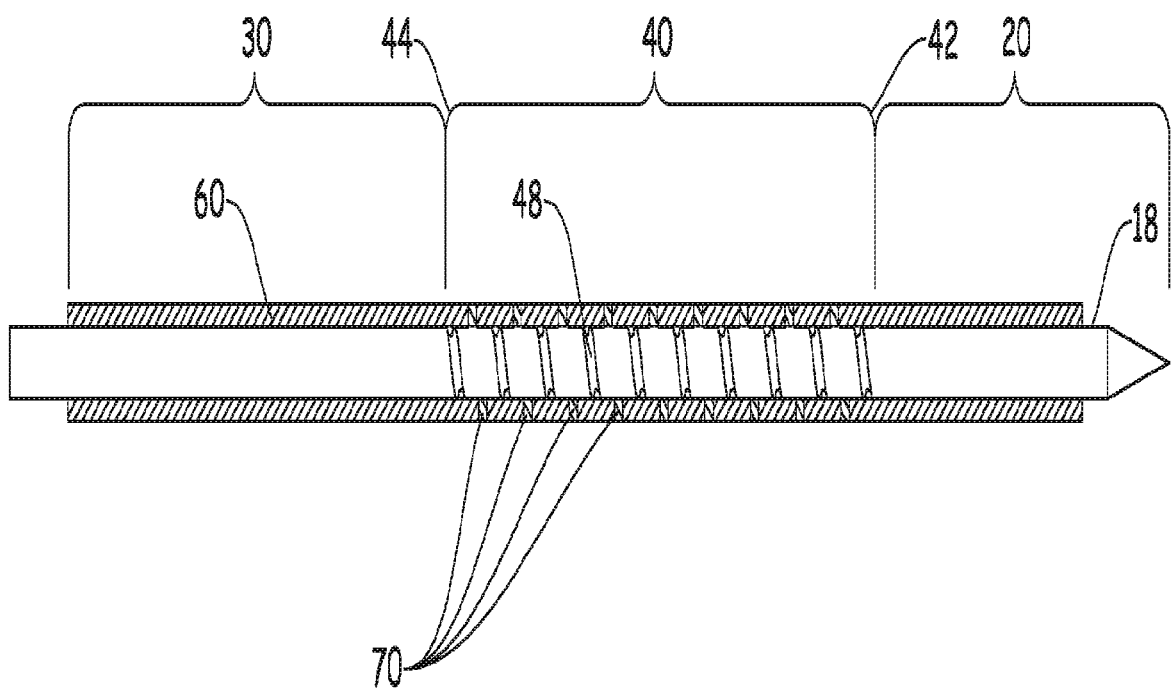
FIG. 2 is a sectional view of a known flexible needle assembly.

In an illustrative example of an assembly without selective decoupling, shown in FIG. 2, a Pebax heat shrink adheres to the hypotube 18 OD over a majority of the length of the Pebax tube. The length of a potential decoupled area of the Pebax is very small. When the hypotube 18 bends, the Pebax has to stretch to accommodate the bend diameter. It is believed that as the tube is bent to greater degrees the strain can become very high and may cause a rupture in the jacketing during use. It is contemplated that if the decoupled region was much larger, the strain on the Pebax would be greatly decreased, which may be expressed in the equation: $E=(L-L_0)/L_0$, E=strain, L=deformed length, $L_0$=decoupled region length. In the prior art and a device without the selectively decoupled regions and having a cut cut, generally $L_0$ equals K. In the present invention, it is contemplated that generally $L_0$ is greater than K. In one preferred embodiment, $L_0$ is at least two times K or $L_0$ is at least the kerf period divided by 2.

It is contemplated in a preferred embodiment, the jacketing member 50 includes one or more coupled regions 60 and one or more decoupled region 70, wherein in at least one or more of the one or more coupled regions 60 are located proximally, distally, or both of at least a portion of the flexible portion 40. In other preferred embodiments, one or more may be true: wherein at least one of the one or more coupled regions 60 are disposed entirely outside of the flexible portion 40; at least one of the one or more coupled regions 60 are disposed within the flexible portion 40; at least one of the one or more decoupled regions 70 are disposed within the flexible portion 40; at least one of the one or more decoupled regions 70 are at least disposed over a cut (e.g. spiral cut feature) 48 and at least laterally away from the cut; a third coupled region 62 is disposed between the one or more coupled regions 60; the coupled region 62 is disposed in-between a spiral cut feature 48, the spiral flex feature disposed within the flexible portion 40.

It is contemplated that a number of methods and techniques may be utilized to enable the creation of selectively decoupled regions. In one example, an additional material may be introduced to the OD of the hypotube 18 in areas where a decoupled region is desired. For example, an expanded PTFE (i.e., ePTFE) film or a layer of inadhesive material could be placed between the hypotube 18 and the longitudinally-fixed layer to prevent adhesion during the heat shrink-wrapping process. Another contemplated method to enable the creation of selectively decoupled regions includes selective heating of the jacketing. It is contemplated that shrinking heat is only applied in areas where coupling is desired. Areas which does not receive sufficient heat to shrink the jacket would remain uncoupled.

It is also contemplated that it may be desirable to have areas or regions that have enhanced coupling between the hypotube 18 and the jacket. It is possible to enhance adhesion or coupling by the use of additional adhesive materials between the hypotube 18 and jacketing. It is also possible to provide additional mechanical joining enhancements such as surface roughness or grain on the metal hypotube 18.

Illustrative Examples

Figure 3:
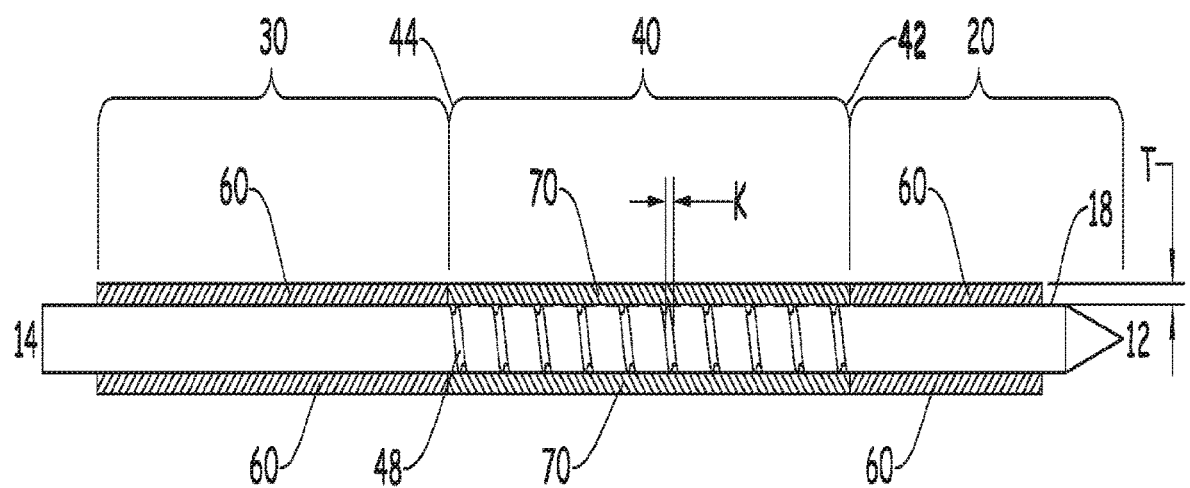
FIG. 3 is a sectional view of one embodiment of the present invention.
Figure 4:
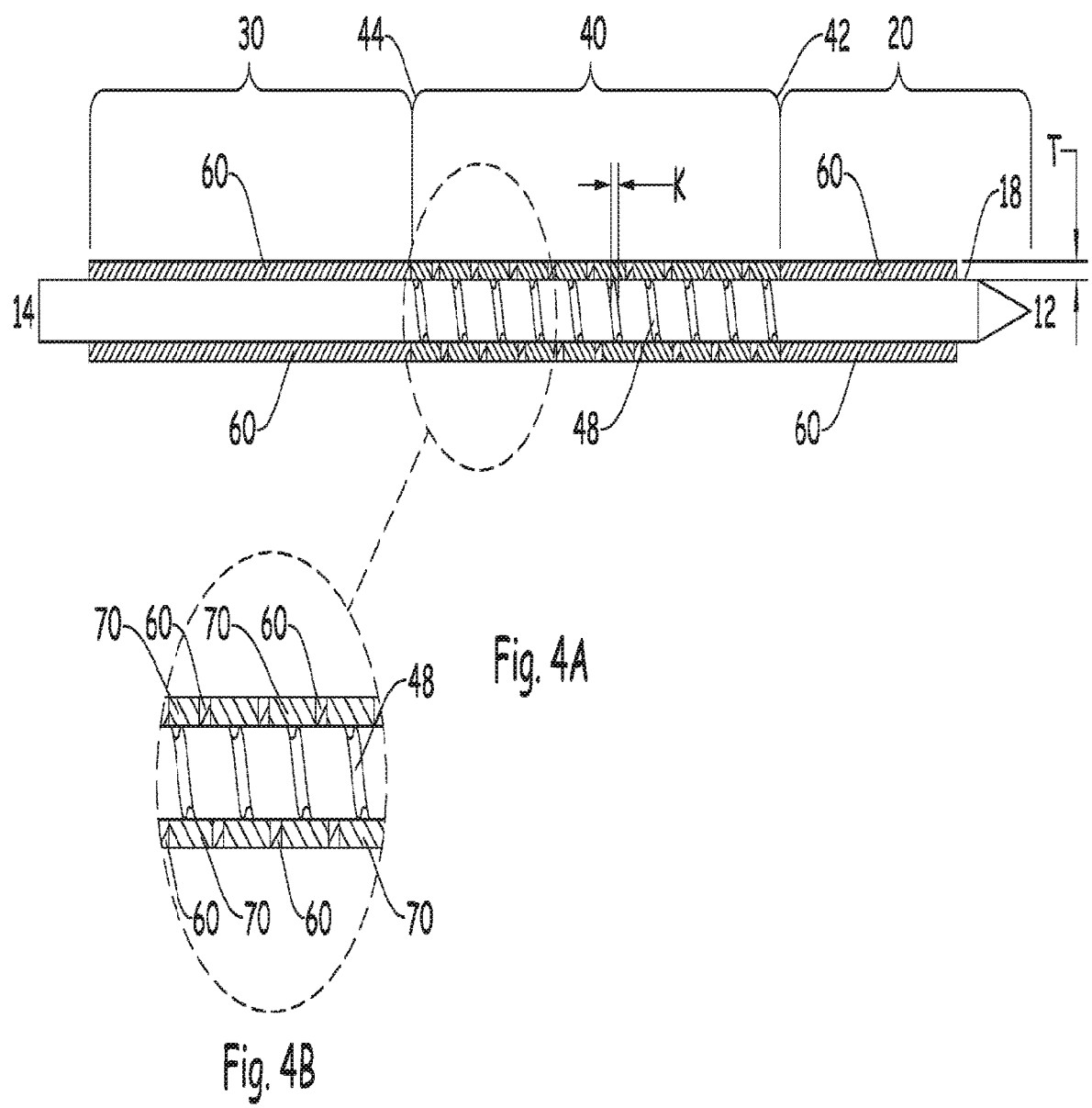
FIG. 4A is a sectional view of another embodiment of the present invention.
FIG. 4B is a close up view of a portion of FIG. 4A.
Figure 5:
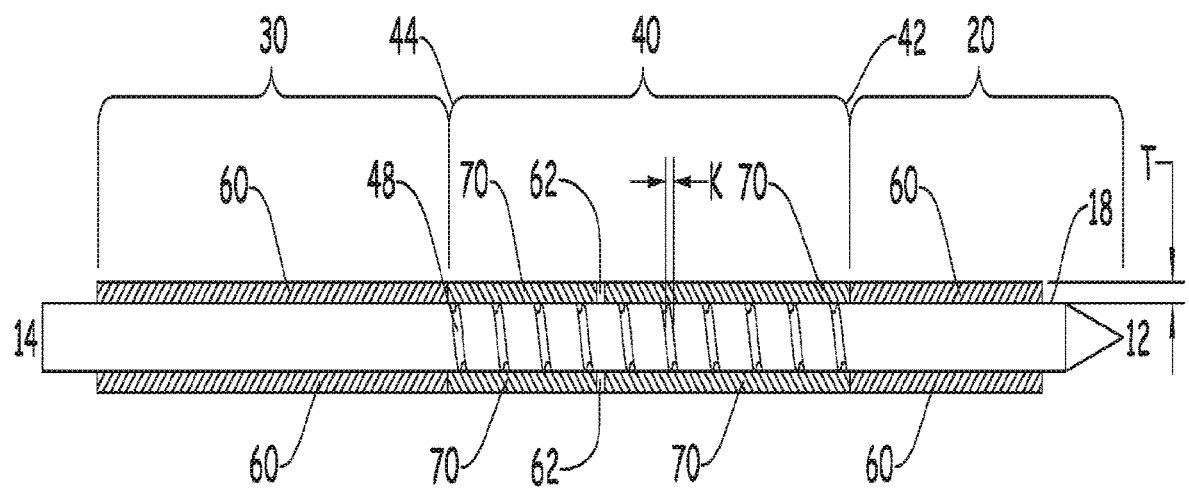
FIG. 5 is a sectional view of yet another embodiment of the present invention.

Illustrative examples may be seen in FIGS. 3-5. These should be regarded only as a limited number examples and is not an exhaustive list of the possible configurations of the present invention.

FIG. 3 show one illustrative example of the present invention. In this figure, the jacket 50 is coupled to the hypotube 18 along the regions surrounding the flexible portion 40 and is decoupled over the entirety of the flexible portion 40. It is contemplated, but not shown, that it may be desirable to extend the decoupled region 70 into the needle portion 20, the stiff portion 30, or both by a specified axial distance away from the cut. It is contemplated that in a preferred embodiment, that this axial distance should be at least equal to about two times the width (K) of the cut.

FIGS. 4A and B shows another illustrative example of the present invention. In this figure, the jacket 50 is coupled to the hypotube 18 along the regions surrounding the flexible portion 40 and is decoupled over a portion of the flexible portion 40. Particularly, the jacket is coupled in the flexible portion 40 at specific areas that lay in-between the cuts, but away from the edge of the cut. In one preferred embodiment, the coupling only takes place at or near the axial mid-point between the cuts as shown in the figure. In an even more preferred embodiment, the axial distance to the edge of coupled region 60 shown is about at least two times the width (K) or half the period of the cut when the cut is a laser cut spiral and lays at or near the midpoint between the cuts. The period of the laser cut spiral may be as small as 0.0005" (0.012 mm).

FIG. 5 shows yet another illustrative example of the present invention. Shown in this figure is a configuration similar to FIG. 3, but including a third coupled region 62 that is disposed within the flexible portion 40. It is contemplated that the third coupled region 62 may be placed any number of places in the flexible portion 40 and may be included to facilitate differing bending characteristics required by the assembly 10. It is contemplated that the third coupled region 62 may be smaller than one section between the cuts (as shown), or may span an area as large as the flexible portion 40.

Unless otherwise stated, any test method standard referenced herein is for the version existing as of the earliest filing date in which the standard is recited.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of, or even consist of the elements, ingredients, components or steps. Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps. Moreover, unless expressly set forth, the recitation of "first", "second", or the like does not preclude additional ingredients, steps, or other elements. All references herein to elements or metals belonging to a certain Group refer to the Periodic Table of the Elements published and copyrighted by CRC Press, Inc., 1989. Any reference to the Group or Groups shall be to the Group or Groups as reflected in this Periodic Table of the Elements using the IUPAC system for numbering groups. It is understood that the above description is intended to be illustrative and not restrictive.

Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

What is claimed is:

1. A medical flexible hypotube assembly, comprising:
a tube including:
 a. a distal portion disposed at a distal end of the medical flexible hypotube assembly, wherein the distal portion comprises a needle;
 b. a stiff portion disposed at a proximal end of the medical flexible hypotube assembly; and
 c. a flexible portion disposed between and interconnecting the distal portion and the stiff portion, wherein the flexible portion includes a flex distal portion and a flex proximal portion, wherein the flexible portion is defined by a cut pattern including cut and uncut portions of the tube; and
a jacketing member disposed about the tube over at least part of the flexible portion;
wherein the jacketing member includes a first coupled region that is coupled to the distal portion of the tube, a second coupled region that is coupled to the stiff portion of the tube, and a decoupled region disposed over a length of the cut and uncut portions of the flexible portion between the first coupled region and the second coupled region.

2. The medical flexible hypotube assembly according to claim 1:
wherein at least one of the first coupled region and the second coupled region are disposed entirely outside of the flexible portion.

3. The medical flexible hypotube assembly according to claim 1:
wherein at least one of the first coupled region and the second coupled region are disposed within the flexible portion.

4. The medical flexible hypotube assembly according to claim 1:
wherein the decoupled region is disposed within the flexible portion.

5. The medical flexible hypotube assembly according to claim 1:
wherein the cut is a spiral cut,
wherein the decoupled region is at least disposed over the spiral cut and away from edges of the spiral cut by an amount greater than 0.0025 mm.

6. The medical flexible hypotube assembly according to claim 1:
wherein the jacketing member includes a third coupled region disposed between the two coupled regions.

7. The medical flexible hypotube assembly according to claim 6:
wherein the third coupled region is disposed in-between cuts in the cut pattern, wherein the third coupled region is spaced a distance from the cuts.

8. The medical flexible hypotube assembly according to claim 1, wherein the decoupled region includes a first longitudinal dimension between a proximal edge and a distal end of the decoupled region and the cut includes a second longitudinal dimension, wherein the first longitudinal dimension is greater than the second longitudinal dimension.

9. A medical flexible hypotube assembly, comprising:
a hypotube comprising:
  a. a distal portion disposed at a distal end of the medical flexible hypotube assembly, wherein the distal portion comprises a needle;
  b. a stiff portion disposed at a proximal end of the medical flexible hypotube assembly; and
  c. a flexible portion disposed between and interconnecting the distal portion and the stiff portion; and
a jacketing member disposed about the hypotube over at least part of the flexible portion;
wherein the jacketing member includes a first coupled region, a second coupled region, and one or more decoupled regions, wherein in the first coupled region is located proximally of the flexible portion and a second coupled region is located distally of the flexible portion,
wherein the flexible portion includes a cut, and
wherein the one or more decoupled regions is disposed over the a cut portion and a non-cut portion of the medical flexible hypotube assembly, and wherein the decoupled region of the jacketing member is decoupled from both the cut portion and the non-cut portion of the medical flexible hypotube.

10. The medical flexible hypotube assembly according to claim 9:
further characterized in that wherein at least one of the one or more coupled regions are disposed entirely outside of the flexible portion.

11. The medical flexible hypotube assembly according to claim 1:
wherein the cut feature is a spiral cut.

12. The medical flexible hypotube assembly according to claim 11:
wherein the decoupled region has a length that is at least two times a width (K) of the spiral cut.

13. The medical flexible hypotube assembly according to claim 11:
wherein the decoupled region has a length that is at least half a period of the spiral cut.

14. The medical flexible hypotube assembly according to claim 9, wherein the one or more decoupled regions include a first longitudinal dimension between a proximal edge and a distal end of the one or more decoupled regions and the cut includes a second longitudinal dimension, wherein the first longitudinal dimension is greater than the second longitudinal dimension.

* * * * *